United States Patent [19]

Masai et al.

[11] Patent Number: 5,426,307
[45] Date of Patent: Jun. 20, 1995

[54] BUNCH YARN INSPECTION METHOD AND DEVICE

[75] Inventors: Tetsuji Masai, Kusatsu; Kenichi Inada, Ohtsu, both of Japan

[73] Assignee: Murata Kikai Kabushiki Kaisha, Kyoto, Japan

[21] Appl. No.: 90,899

[22] Filed: Jul. 12, 1993

[30] Foreign Application Priority Data

Jul. 14, 1992 [JP] Japan .................. 4-187005

[51] Int. Cl.⁶ .......................................... G01N 21/64
[52] U.S. Cl. .............................. 250/461.1; 250/459.1
[58] Field of Search ............... 250/458.1, 469.1, 461.1

[56] References Cited

U.S. PATENT DOCUMENTS 4,877,967 10/1989 Kawamura ...................... 250/459.1

Primary Examiner—Carolyn E. Fields
Attorney, Agent, or Firm—Spensley Horn Jubas & Lubitz

[57] ABSTRACT

An inspection device for inspecting a bunch yarn winding wound on a take up tube of a package. A black light is provided for irradiating the bunch yarn winding with light having a wavelength substantially in the ultra violet range, and a CCD camera is provided for sensing and inspecting the irradiated bunch yarn winding.

8 Claims, 3 Drawing Sheets

BUNCH YARN INSPECTION METHOD AND DEVICE

BACKGROUND OF THE INVENTION

1. Field of the Invention

The present invention relates to a package inspection device for inspecting bunch wound yarn wound onto a take up tube.

2. Prior Art

The package wound by the take up winder is bunch wound on the take up tube and then formed into a package.

In recent years, instead of cardboard tubes, resin tubes are being used in take up tubes and they are often brightly coloured, for example, yellow or pink.

Various means of package inspection take place to see if the package has been correctly wound or not.

In conventional inspection of bunch wound yarn, a white light irradiates the bunch wound yarn which is scanned by a CCD camera, and the bunch wound yarn is inspected by means of image processing.

However, because the take up tube is brightly coloured as mentioned above, if the take up tube and the bunch wound yarn are scanned by the CCD camera, it is difficult to show a clear contrast between them. Further, because the take up tube contains a number of small lumps or protuberances which stop the yarn slipping easily, even when there is no bunch wound yarn, it is easy to detect these small protuberances as the bunch wound yarn by mistake, so that inspection cannot be done accurately.

For this reason, the present invention seeks to overcome the above problems and to provide a package inspection device which is capable of accurately distinguishing bunch wound yarn and the take up tube for bunch wound yarn inspection.

SUMMARY OF THE INVENTION

In order to achieve the abovementioned purpose, this invention is a package inspection device for inspecting bunch wound yarn wound on a take up tube of a package characterised in that it composes a black light which irradiates a light having a wave length close to that of ultra violet rays for the take up tube and a CCD camera which scans and inspects the irradiated bunch wound yarn.

According to the above composition, if a black light having a wave length close to that of ultra violet rays is irradiated for a take up tube and a bunch wound yarn, the bunch wound yarn emits fluorescence. Therefore the bunch wound yarn can be distinguished from the take up tube and accurate inspection can take place.

DETAILED DESCRIPTION OF PREFERRED EMBODIMENT

The following is a description of the present invention according to a preferred embodiment and attached drawings.

Figure 1:
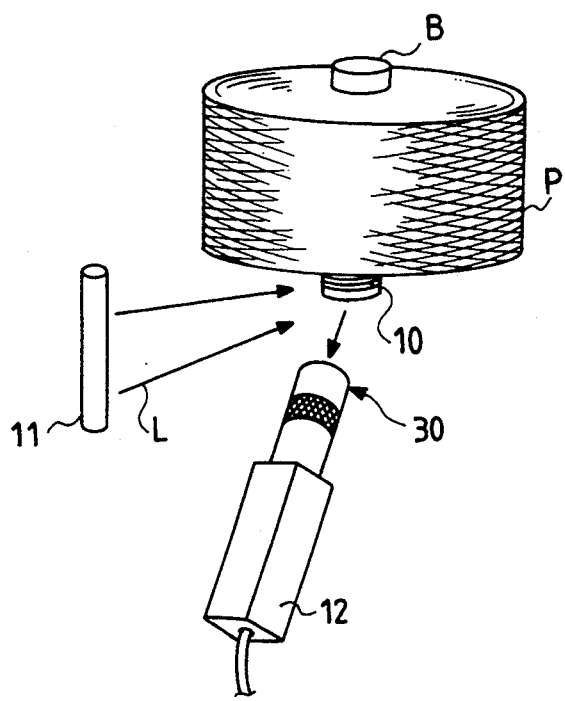
FIG. 1 shows a diagonal view of an outline of a preferred embodiment of the present invention.

In FIG. 1 a bunch wind 10 is wound onto a take up tube B of the package P and, although not shown in the drawing, the take up tube B stands upright in the tray. This package P is, for example, conveyed into a package inspection box along a conveyor path and the inspection of the present invention and other types of inspection relating to the package take place in the inspection box.

A black light lamp 11 for irradiating the bunch wind 10 on the take up tube B and a CCD camera 12 for inspecting the bunch wind 10 are arranged in the inspection box. The black lamp 11 irradiates light which has a wavelength close to that of ultra violet rays, for example, ultra violet rays L having a wave length of 350 nm. Further, when the irradiation of the black light and the scanning by the CCD camera 12 are carried out, the whole package P is inside the inspection box which is a dark box.

In the above, if light in the region of ultra violet rays is irradiated by lamp 11 onto the part of the take up tube B on which the bunch wind 10 is wound, the yarn layers of the bunch wind 10 emit a fluorescent light, although the take up tube B does not emit a fluorescent light. Therefore, when the CCD camera 12 scans this, the contrast between the take up tube B and the bunch wind 10 is clear and regardless of the protuberance and the colour of the resin take up tube, a high S/N (signal/-noise ratio) signal can be gained and it can be easily determined whether the bunch wind has been completed successfully or not.

Figure 2:
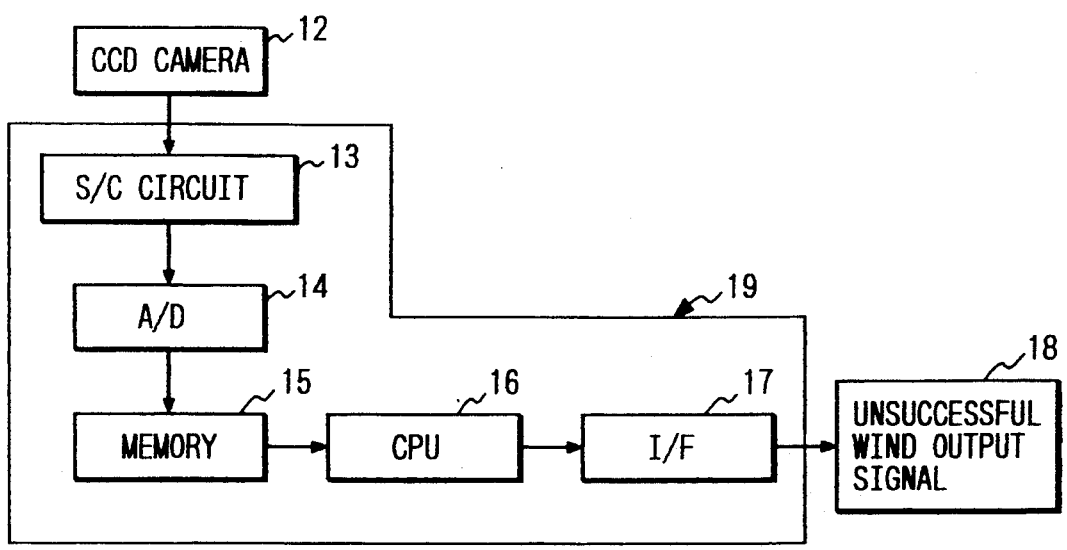
FIG. 2 shows the determination circuit which determines by means of the signal coming from the CCD camera whether the bunch wound yarn has been wound successfully or not.
Figure 3A:
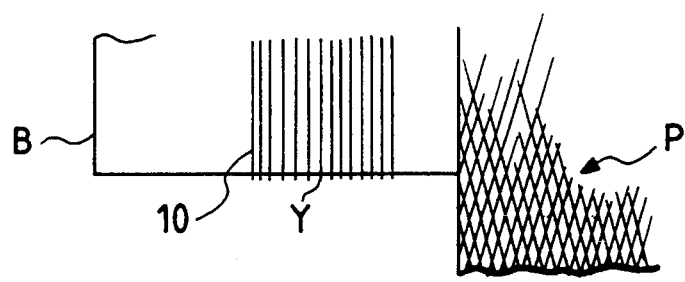
FIGS. 3a, 3b and 3c show the scanning portion of the bunch wind portion of the package and the signal and processing signal of the CCD camera.
Figure 3B:
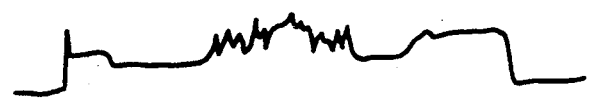
Figure 3C:
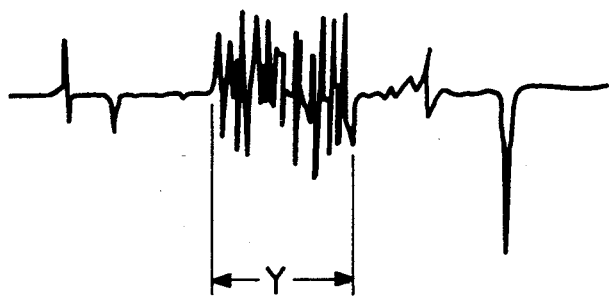

FIG. 2 shows the determination circuit 19 in which the success or otherwise of the bunch wind 10 is determined by the signal from the CCD camera 12 and FIGS. 3a, 3b and 3c show the CCD camera signal etc. corresponding to the part of the take up tube on which the bunch wind 10 is wound.

Firstly, as shown in FIG. 3a, there are yarn layers Y of bunch winds 10 on the take up tube B and these are scanned by the CCD camera 12. As shown in FIG. 3b the CCD camera 12 signal does not change between the end of the take up tube B and the bunch wind 10 but changes at the yarn layers Y. If this CCD camera 12 signal is processed at the signal conditioner circuit 13 as shown in FIG. 2, as shown in FIG. 3c the CCD camera signal is amplified. Whether the yarn layers Y have been wound successfully or not can be determined by this amplified signal.

In other words, as shown in FIG. 2, the signal conditioner circuit 13 signal is converted into a digital signal at the A/D conversion circuit 14 and stored in the memory 15. As shown in FIGS. 3a, 3b and 3c, whether the bunch wind 10 yarn layers have been successfully wound or not, i.e., there are no yarn layers Y or the yarn layers Y have not reached the predetermined width, is determined according to the data stored in the memory 15 by the CPU 16, and if the CPU 16 determines that the bunch wind 10 have not been successfully wound, the CPU 16 outputs via the interface 17 an unsuccessful wind output signal 18.

In other words, according to the above invention, when light which has a wave length close to that of ultra violet rays is irradiated from a black lamp to the part of the take up tube wound with the bunch wind, the bunch wound yarn emits a fluorescence and can be distinguished from the take up tube. Therefore, accurate inspection can take place.

Figure 4:
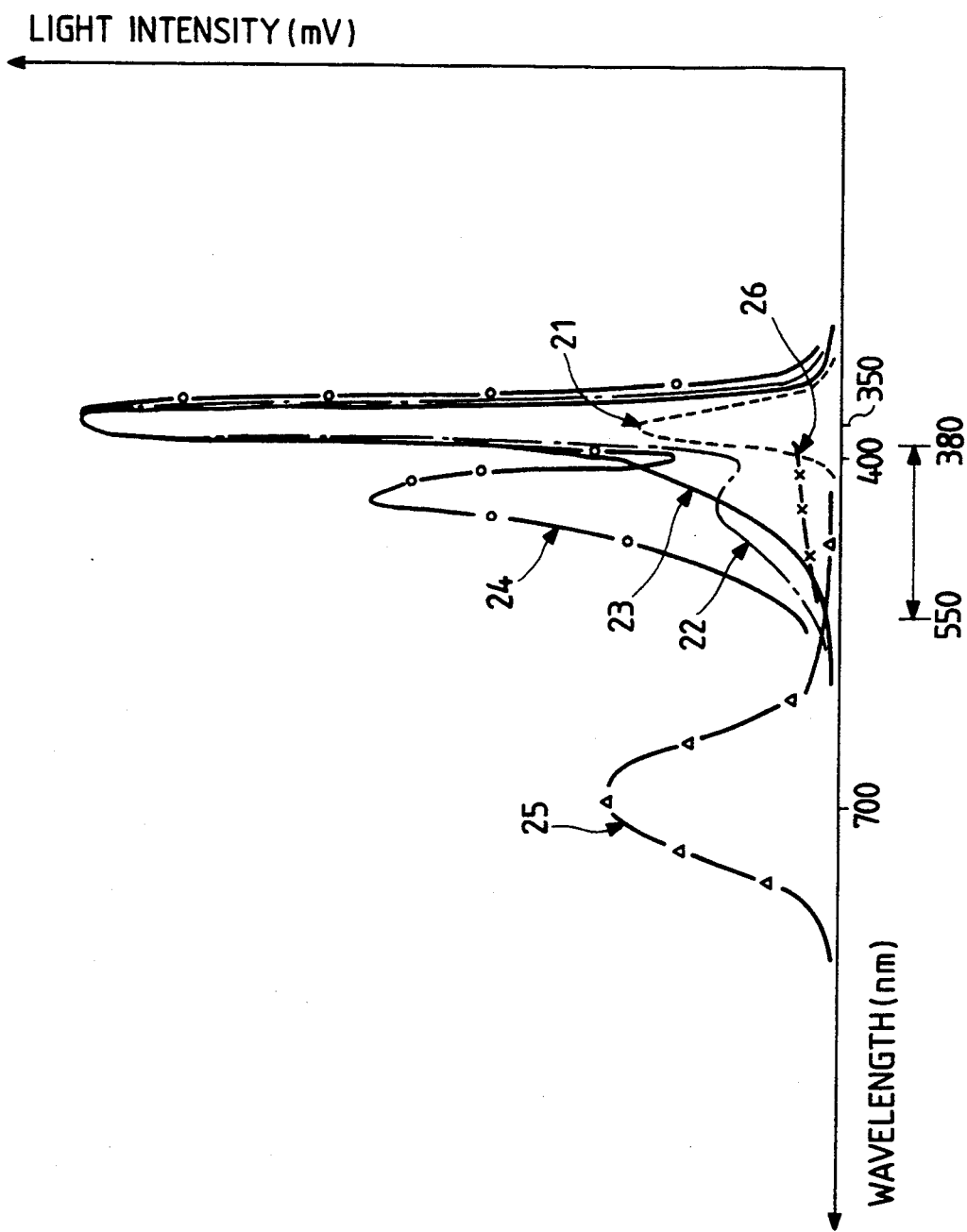
FIG. 4 is the graph showing the spectro characteristics of the yarn.

Furthermore, the following is a detailed explanation of the present invention. FIG. 4 shows the spectro characteristics of the yarn. The horizontal axis represents wave length and the vertical axis represents light intensity. 22 shows the characteristics of the cotton yarn, 23 shows the characteristics of polyester and cotton blend yarn, 24 shows the characteristics of rayon yarn, 21 shows black light and 25 shows white light. As can be seen in the graph, the characteristics of the yarn vary according to the type of yarn. However, whether yarn type 22, 23 or 24, the light intensity shows a high value within a wave length region of about 300 to 550 nm. As to the black light 21, the light intensity shows a high value within the wave length region of about 330 to 400 nm. On the other hand, as to the white light 25, the light intensity shows a high value within the wave length region of about 600 to 800 nm and shows a low value below 600 nm. As a result, even if the white light 25 is irradiated to the yarns 22, 23 and 24, the yarns 22, 23 and 24 do not emit fluorescence. However, if black light 21 is irradiated to yarns 22, 23, 24, the yarns 22, 23 and 24 emit fluorescence.

As shown in FIG. 1, black light is irradiated onto the bunch wind portion of the take up tube and the bunch wind portion is scanned by means of the CCD camera 12. Furthermore, on the lens of the CCD camera 12 a filter 30 is attached which limits the analysis region to the wave length region of 380 to 550 nm. The take up tube which is used is one which has a light intensity showing a low value within the wave length region of 380 to 550 nm. In FIG. 4, 26 shows the spectro characteristics of the take up tube B.

Because the filter 30 is attached to the lens of the CCD camera 12, the light which has a wavelength of about 400 nm is actually detected. In 400 nm wavelength, as in FIG. 4, the light intensity of the yarns 22, 23 and 24 show a high value and the light intensity of the tube 26 shows a low value. As a result, the yarns 22, 23 and 24 emit fluorescence but the take up tube 26 does not, so that the bunch wind 10 can be accurately inspected. As can be understood from FIG. 4, light which can be irradiated is not limited to black light and so long as the light has a wave length region in which the light intensity shows a high value when the light is irradiated on the yarn, it will irradiate. Although it is desirable to use a light in which a disparity of the light intensity between the yarn and tube is generated, the filter 30 may be used to limit the wave length to within the region in which a disparity of light intensity between the yarn and tube will be generated.

What is claimed is:

1. A method for inspecting bunch wound yarn wound on a take up tube, the method comprising:
   irradiating the take up tube and the bunch wound yarn with light, the light having a wavelength within a range at which fluorescent light emitted from the bunch wound yarn will exhibit a relative peak in intensity when irradiated by the light,
   detecting the intensity of light emitted by the bunch wound yarn and the take up tube, and
   distinguishing the bunch wound yarn and the take up tube based upon differences in intensity.

2. The method of claim 1, wherein the step of irradiating the take up tube and the bunch wound yarn with light comprises the step of irradiating the take up tube and the bunch wound yarn with light having a wavelength within a range at which fluorescent light emitted from the bunch wound yarn will exhibit a first intensity, wherein light emitted by the take up tube will exhibit a second intensity, and wherein the first and second intensities are different.

3. The method of claim 1, wherein the step of detecting the intensity of light emitted by the bunch wound yarn and the take up tube comprises the step of filtering the light emitted by the bunch wound yarn and the take up tube using a filter which transmits light having a wavelength within a predetermined range.

4. A device for inspecting bunch wound yarn wound on a take up tube, comprising
   irradiation means for irradiating the take up tube and the bunch wound yarn with light, the light having a wavelength within a range at which fluorescent light emitted from the bunch wound yarn will exhibit a relative peak in intensity when irradiated by the light, and
   detection means for detecting the intensity of light emitted by the bunch wound yarn and the take up tube, and
   means for distinguishing the bunch wound yarn and the take up tube based upon differences in intensity.

5. The device of claim 4, wherein the irradiation means comprises a lamp which radiates black light and the detection means comprises a CCD camera.

6. The device of claim 5, wherein the detection means comprises a filter which transmits light having a wavelength within a predetermined range for filtering the light emitted by the bunch wound yarn and the take up tube.

7. A method for inspecting bunch wound yarn wound on a take up tube, the take up tube comprising at least one of a synthetic resin and a material having protrusions on an outer surface thereof, the method comprising:
   irradiating the take up tube and the bunch wound yarn with light, the light having a wavelength within a range at which fluorescent light emitted from the bunch wound yarn will exhibit a relative peak in intensity when irradiated by the light,
   detecting the intensity of light emitted by the bunch wound yarn and the take up tube, and
   distinguishing the bunch wound yarn and the take up tube based upon differences in intensity.

8. A device for inspecting bunch wound yarn wound on a take up tube, the take up tube comprising at least one of a synthetic resin and a material having protrusions on an outer surface thereof, comprising
   irradiation means for irradiating the take up tube and the bunch wound yarn with light, the light having a wavelength within a range at which fluorescent light emitted from the bunch wound yarn will exhibit a relative peak in intensity when irradiated by the light, and
   detection means for detecting the intensity of light emitted by the bunch wound yarn and the take up tube, and
   means for distinguishing the bunch wound yarn and the take up tube based upon differences in intensity.

* * * * *